(12) United States Patent
Hartwig et al.

(10) Patent No.: US 8,393,589 B2
(45) Date of Patent: Mar. 12, 2013

(54) CONTAINER SUPPORT DEVICE

(75) Inventors: Rainer Hartwig, Hambuhren (DE); Gunter Heeke, Gottingen (DE); Matthias Gretzinger, Hannover (DE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 35 days.

(21) Appl. No.: 12/950,680

(22) Filed: Nov. 19, 2010

(65) Prior Publication Data

US 2011/0284295 A1 Nov. 24, 2011

Related U.S. Application Data

(63) Continuation of application No. 10/670,445, filed on Sep. 25, 2003, now Pat. No. 7,837,167.

(51) Int. Cl.
*A47H 99/00* (2009.01)
(52) U.S. Cl. .................. 248/299.1; 248/324; 248/284.1
(58) Field of Classification Search ............ 248/222.51, 248/222.52, 299.1, 324, 291.1, 294.1, 284.1; 177/245, 253, 262, 264
See application file for complete search history.

(56) References Cited

U.S. PATENT DOCUMENTS

| | | | |
|---|---|---|---|
| 1,999,312 A | 4/1935 | Zeissl | |
| 2,552,758 A | 5/1951 | Andersen | |
| 3,191,663 A | 6/1965 | Bieschke | |
| 3,712,394 A * | 1/1973 | Davies et al. | 177/1 |
| 3,750,994 A | 8/1973 | Bieschke | |
| 3,894,593 A * | 7/1975 | Hall et al. | 177/164 |
| 3,944,180 A | 3/1976 | Rogers | |
| 4,019,770 A | 4/1977 | Poelma | |
| 4,425,975 A * | 1/1984 | Luchinger | 177/50 |
| 4,573,655 A | 3/1986 | Vulic | |
| 5,165,647 A | 11/1992 | Ribeiro | |
| 5,352,056 A | 10/1994 | Chandler | |
| 5,366,406 A * | 11/1994 | Hobbel et al. | 452/179 |
| 5,367,129 A * | 11/1994 | Lahl, Jr. | 177/229 |
| 5,445,610 A | 8/1995 | Evert | |
| 5,836,548 A | 11/1998 | Dietz | |
| 5,856,637 A * | 1/1999 | Vande Berg | 177/145 |
| 5,927,780 A | 7/1999 | Chandler | |
| 6,189,834 B1 | 2/2001 | Diet | |
| 6,509,534 B1 * | 1/2003 | Thadani | 177/126 |

(Continued)

FOREIGN PATENT DOCUMENTS

EP 0543440 5/1993
GB 0103409 11/1916

(Continued)

OTHER PUBLICATIONS

Written Opinion of the International Searching Authority for corresponding Intl. Appln. No. PCT/EP2004/010840.

(Continued)

*Primary Examiner* — Terrell McKinnon
*Assistant Examiner* — Steven Marsh
(74) *Attorney, Agent, or Firm* — K&L Gates LLP

(57) ABSTRACT

A blood cleansing system includes: a weight scale; a container support device for supporting a container of a blood treating fluid, wherein the container support device includes: an attachment member for coupling the container support device to the weight scale; a joint body attached to the attachment member and configured to rotate about an axis of the attachment member; a support body secured to the joint body; and at least one container support extending from the support body, wherein the container support is configured to stably support the fluid container.

12 Claims, 5 Drawing Sheets

U.S. PATENT DOCUMENTS 6,582,349 B1 * 6/2003 Cantu et al. .................. 494/1
6,634,611 B1 10/2003 Shih
6,708,940 B2 3/2004 Ligertwood

FOREIGN PATENT DOCUMENTS

GB 1588512 4/1981
RU 494618 5/1975

OTHER PUBLICATIONS

International Preliminary Report on Patentability mailed Mar. 27, 2006 for corresponding Intl. Appln. No. PCT/EP2004/010840.
European Office Action issued Aug. 14, 2012, for corresponding European Appln. No. 04 787 034.0-2320.

* cited by examiner

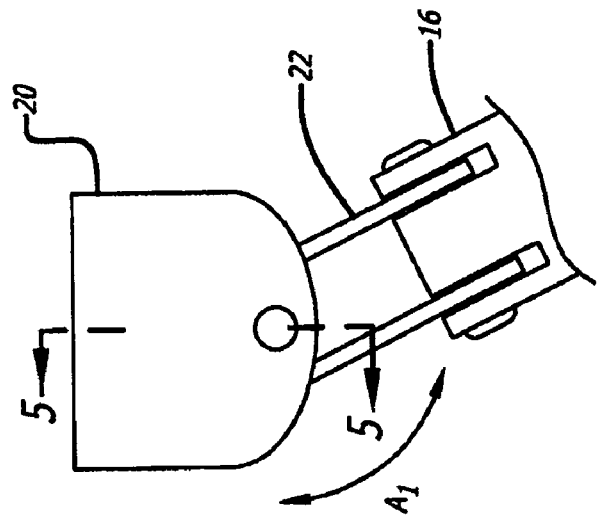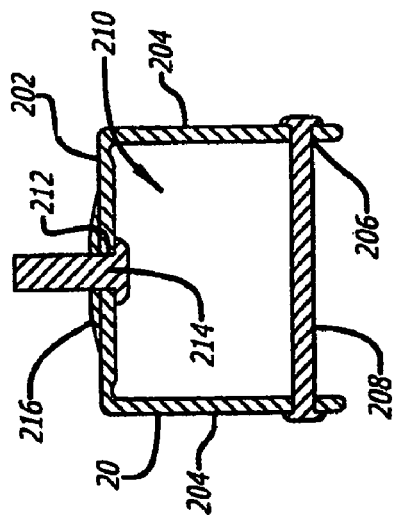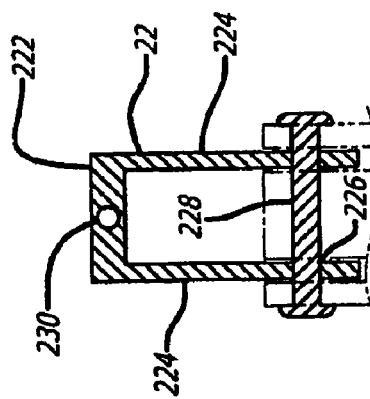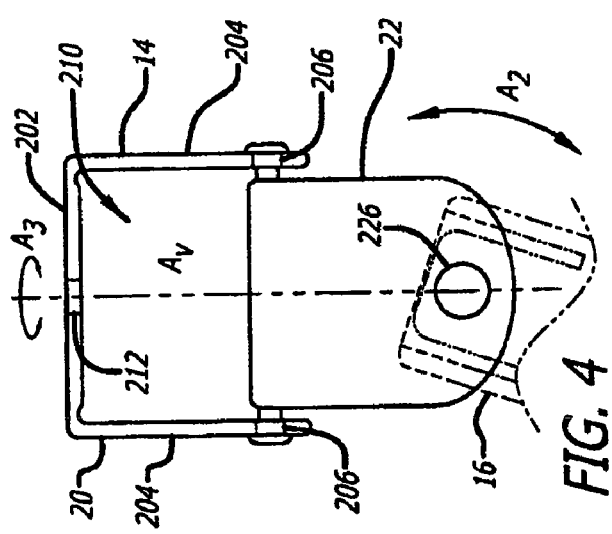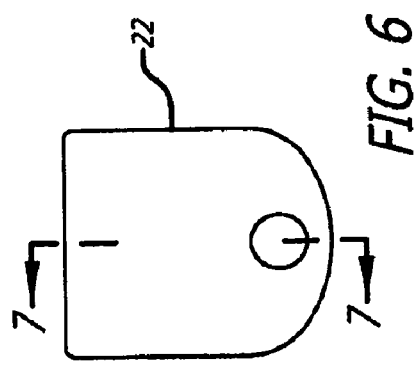

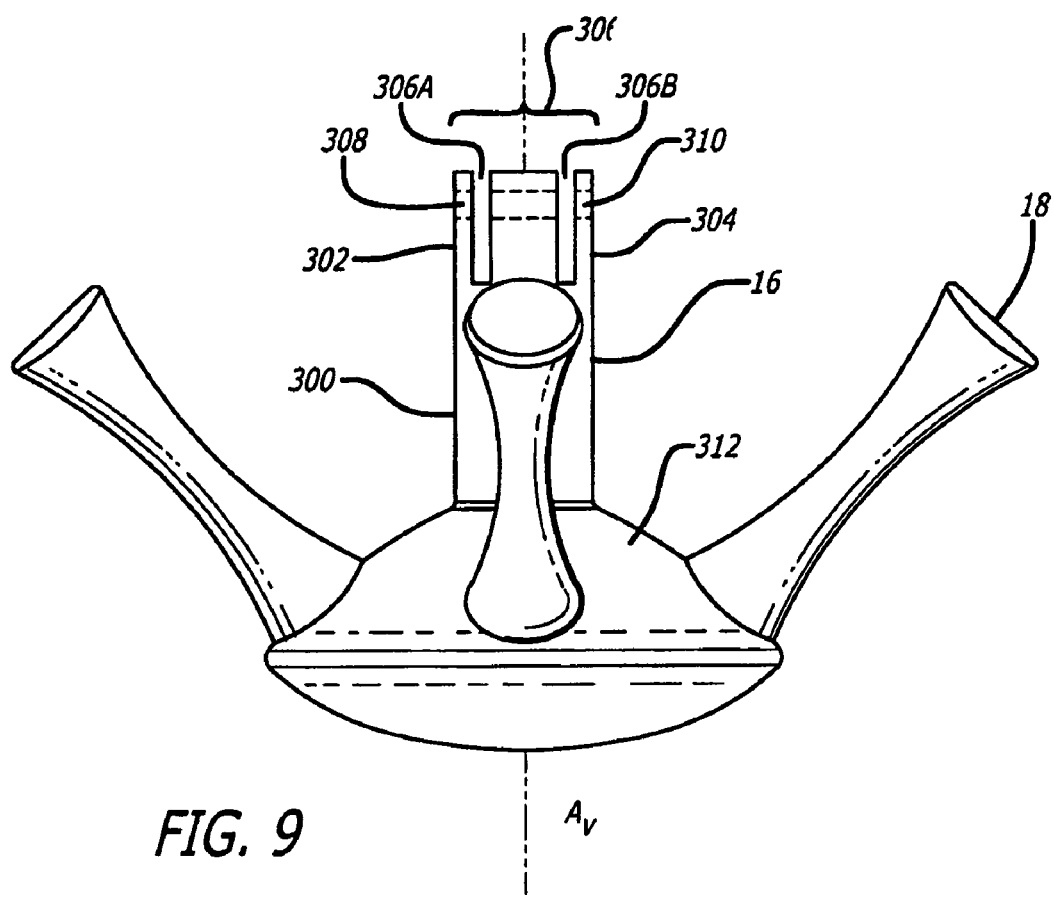
FIG. 9
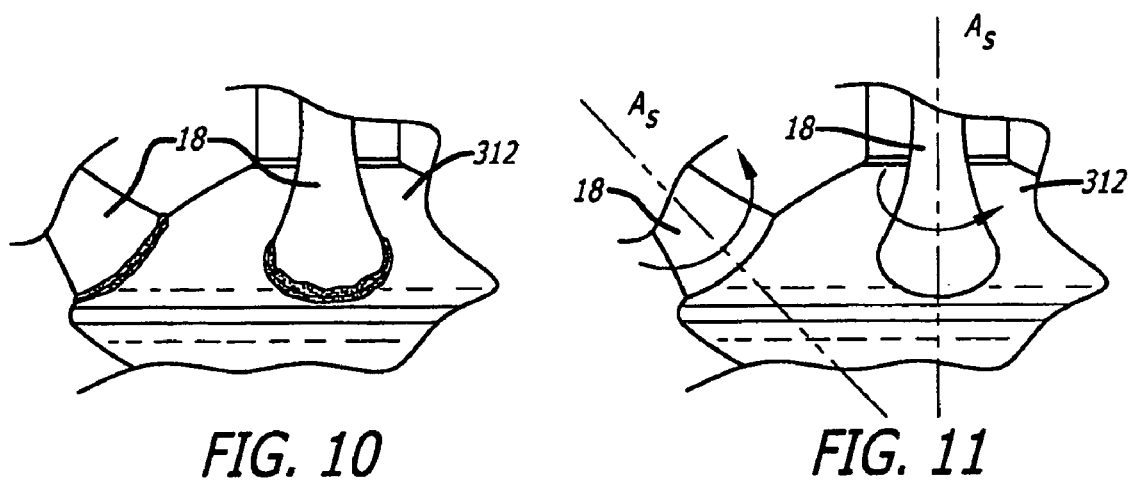
FIG. 10
FIG. 11

FIG.12
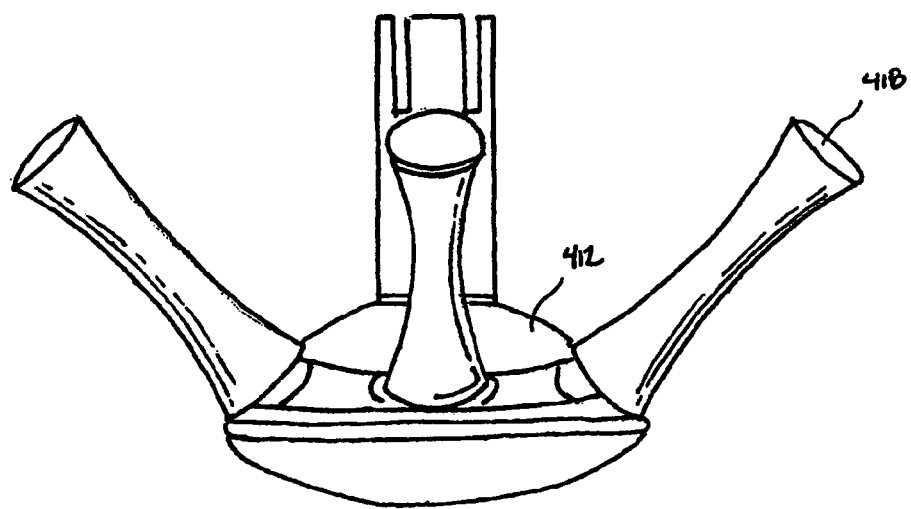
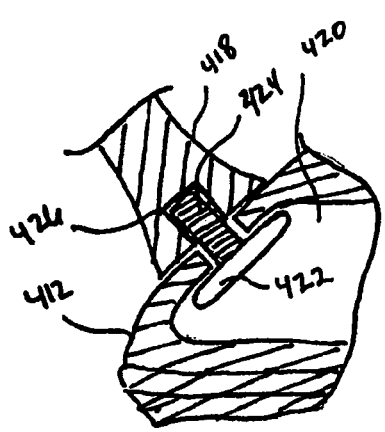
FIG. 13
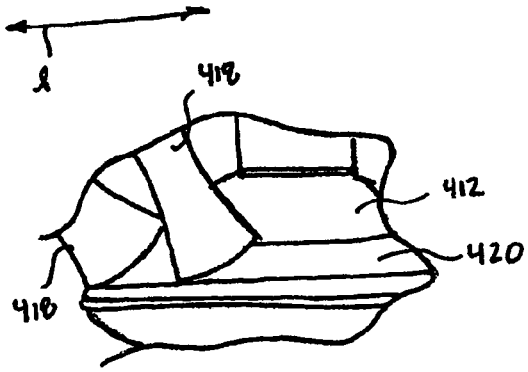
FIG. 14

CONTAINER SUPPORT DEVICE

PRIORITY CLAIM

This application is a continuation of, claims priority to and the benefit of U.S. patent application Ser. No. 10/670,445, filed on Sep. 25, 2003, the entire contents of which are incorporated herein by reference and relied upon.

BACKGROUND

In a variety of medical procedures various fluids may be added to or removed from the circulatory or other physiological systems of a patient. For example, a number of blood filtration and extra-renal replacement therapies remove and filter blood and other fluids from the circulatory or renal systems of a patient and return treated fluids or replacement fluids to the patient. For example, therapies based on haemofiltration, haemodialysis, haemodiafiltration, and plasmatheresis remove and replace a quantity of fluids from a patient. During these procedures, the quantity of fluids removed from and delivered to the patients must be closely monitored. For example, the delivery of a greater amount of fluid to the patient than was removed may result in unnecessary organ strain or, in the case of blood therapies, high blood pressure. In contrast, the delivery of a lesser amount of fluid to the patient than was removed may result in low blood pressure, dehydration, organ failure, or a host of other related medical complications.

A number of fluid replacement devices which incorporate one or more scales configured to control flow pumps and to regulate the delivery of fluids to and from a patient have been developed. Typically, these systems utilize a first weight scale to weigh the amount of fluid being removed from a patient and a second weight scale to weigh the amount of fluid being delivered to the patient simultaneously. While these systems have proven successful in the past, a number of shortcomings have been identified. For example, multiple scale systems are complex devices which have been proven difficult and time-consuming to calibrate. In addition, systems utilizing multiple scales require an operator to precisely monitor multiple weighting systems whose measurements are constantly changing during a particular procedure.

In response, alternate systems utilizing a single weight scale have been developed. These single scale systems measure and balance the quantity of fluid removed from and delivered to the patient simultaneously. Typically, a container support device having multiple container supports thereon is coupled to the weight scale. An empty container for receiving fluid from the patient and a container having delivery fluids therein are positioned on and essentially balanced on the container support device. Thereafter, supply lines are coupled to each container and pumps, usually peristaltic pumps, are coupled to the supply lines. During use, the pumps remove fluid from and deliver fluid to the patient simultaneously. Ideally, at all times during the procedure combined weight of the two containers remains substantially constant. The weight scale having the container support device coupled thereto constantly monitors the combined weight of the two containers during the procedure. During use, should the combined weight of the two containers vary beyond a predetermined limit an alarm will be triggered and the pumps connected to the containers will cease operation. In contrast to multiple scale systems, single scale systems are easier to operate and require considerably less time to calibrate than multiple scale systems. However, at least one shortcoming associated with both systems stems from inaccuracies in the weighting process. Torque or tortional constraints present within the weighting systems may affect weight measurement accuracy. In addition, balancing and calibrating present systems is a time consuming and labor intensive process. Furthermore, the ability of present systems to support multiple delivery containers (e.g. 3 or more containers) has proven problematic. More specifically, monitoring and balancing one container for receiving fluid from the patient and one container for delivering replacement fluids to the patient has been accomplished with some success. However, monitoring and balancing one container for receiving fluid from the patient and multiple containers for delivering replacement fluids to the patient has proven to be more problematic.

Thus, in light of the foregoing, there is an ongoing need for a container support system adapted to couple to a material weighting device and capable of supporting and balancing multiple containers during a medical procedure.

SUMMARY

A container support device for supporting one or more material containers while removing fluids from and delivering one or more therapeutic agents to a patient is disclosed. The container support device disclosed herein may be coupled to a variety of weight scales or measuring devices. For example, the container support device may be affixed to a scale coupled to a fluid substitution device for use in providing a substitution fluid to a patient. Optionally, the container support device may be affixed to a scale coupled to a fluid removal device configured to remove at least one fluid from the body of a patient.

In one exemplary embodiment, a container support device is disclosed and includes an attachment member for coupling the container support device to a weight scale, a joint body attached to the attachment member and configured to rotate about a vertical axis thereof, a support body secured to the joint body, and at least one container support extending from the support body.

In another exemplary embodiment, a container support device is disclosed and includes an attachment member for coupling the container support device to a weight scale, a joint body attached to the attachment member and configured to rotate about a vertical axis thereof, a support body secured to and configured to rotate about the vertical axis of the joint body, and at least one container support extending from the support body.

In yet another exemplary embodiment, a container support device is disclosed and includes an attachment member for coupling the container support device to a weight scale, a joint body attached to the attachment member and configured to rotate about a vertical axis thereof, the joint body having a first joint member configured to couple to the attachment member in rotatable relation thereto and a second joint member configured to couple to the first joint member, a support body movably coupled to the second joint member, and at least one container support extending from the support body.

In still another exemplary embodiment, a container support device is disclosed and includes an attachment member for coupling the container support device to a medical fluid replacement device, a joint body attached to the attachment member and configured to rotate about a vertical axis thereof, the joint body having a first joint member configured to couple to the attachment member in rotatable relation thereto and a second joint member configured to couple to the first joint member and move along a first arc $A_1$, a support body movably coupled to the second joint member and configured to move along a second arc $A_2$, and at least two container supports extending from the support body. Such container supports may be positioned to be equidistant from the vertical axis of the joint body and arc $A_2$ may be perpendicular to arc $A_1$.

Additional features and advantages are described herein, and will be apparent from the following Detailed Description and the figures.

BRIEF DESCRIPTION OF THE FIGURES

Various exemplary embodiments of a container support device will be explained in more detail by way of the accompanying drawings, wherein components having similar but not necessarily the same or identical features, may have the same reference numeral, and wherein:

FIG. 4 shows a side view of an embodiment of a joint body of a container support device having a first joint member and a second joint member attached thereto;

FIG. 5 shows a cross sectional view of an embodiment of a first joint member of a joint body as viewed along the lines 5-5 shown in FIG. 8;

FIG. 6 shows a side view of an embodiment of a second joint member of a joint body;

FIG. 7 shows a cross sectional view of an embodiment of a second joint member of a joint body as viewed along the lines 7-7 of FIG. 6;

FIG. 8 shows an embodiment of a joint body of a container support device having a support body coupled to a second joint member;

FIG. 9 shows a side view of an embodiment of a support body of a container support device having container supports coupled thereto;

FIG. 10 shows a side view of an embodiment of a container support of a support body wherein the container support is non-rotatably fixed to a container support body;

FIG. 11 shows a side view of an embodiment of a container support of a support body wherein the container support is rotatably fixed to a container support body;

FIG. 12 shows a side view of an embodiment of a support body of a container support device having container supports movably coupled thereto;

FIG. 13 shows a side view of an embodiment of a container support having a coupling member positioned within a container support channel formed on a support body; and FIG. 14 shows a side view of an embodiment of a container support of a support body wherein two container supports are positioned proximate to each other and movably coupled to the support body.

DETAILED DESCRIPTION

Figure 1:
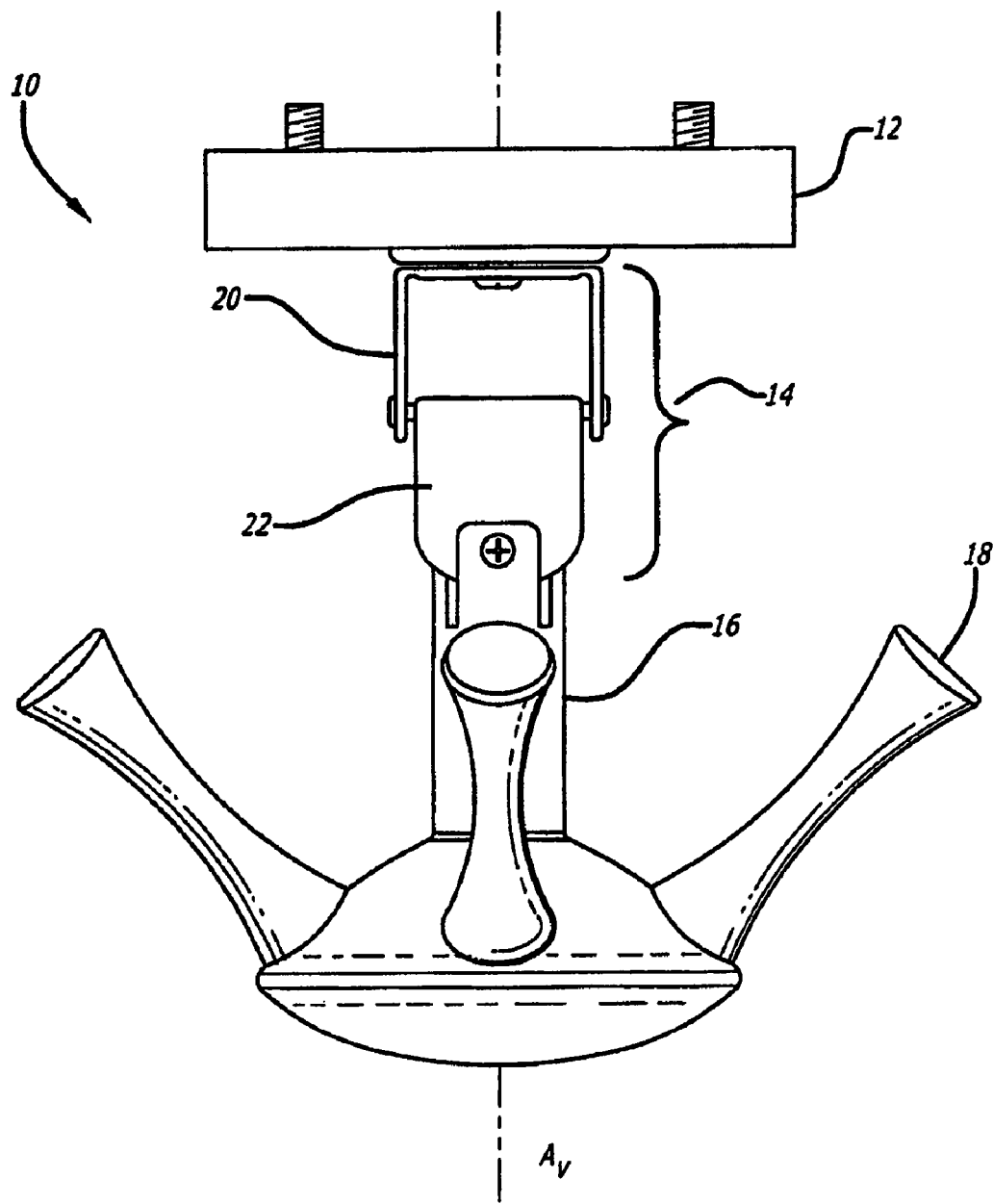
FIG. 1 shows a side view of an embodiment of a container support device having an attachment member, a joint body coupled to the attachment member, and a container support body coupled to the joint body.

FIG. 1 shows one exemplary embodiment of a container support device. As shown, the container support device 10 includes an attachment member 12 coupled to a joint body 14. A support body 16 having one or more container supports 18 thereon is coupled to the joint body 14. In the illustrated embodiment the joint body 14 includes a first joint member 20 and a second joint member 22. Optionally, any number of joint members may be utilized to form the joint body 14. As shown, the joint body 14 and the support body 16 are colinearly positioned along the vertical axis $A_V$. In an alternate embodiment, the joint body 14 and the support body 16 may not be positioned along a common vertical axis. The container support device 10 or the various components thereof may be manufactured in a variety of sizes and configured to engage and support a variety of material containers. For example, in one embodiment, the container support device 10 may have a length of device for extracting fluids from and delivering fluids to a patient, such as systems dedicated to blood filtration therapies, extra-renal replacement therapies, and the like. Exemplary containers for coupling to the container support device 10 include, without limitation, bags, pouches, bottles, cups, buckets, boxes, and similar devices. In addition, the container support device 10 or the various components thereof may be manufactured from a variety of materials including, for example, stainless steel, titanium, various metallic alloys, aluminum, ceramic materials, plastics, elastomers, silicones, or a combination thereof.

Figure 2:
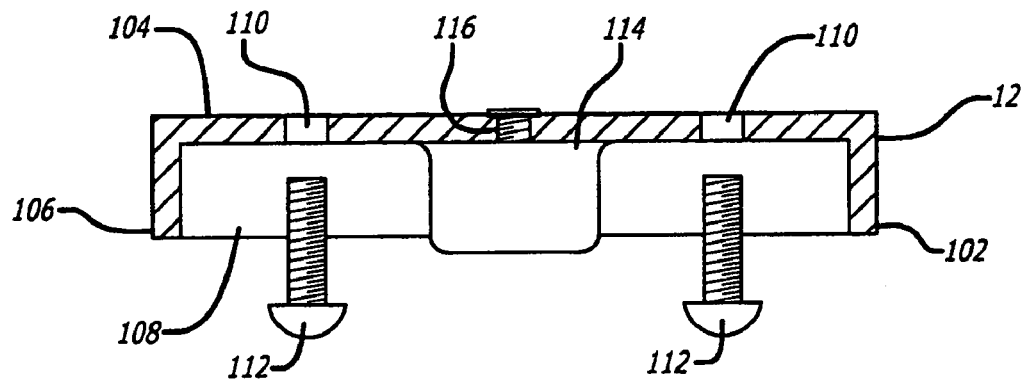
FIG. 2 shows a cross sectional view of an embodiment of an attachment member of a container support device as viewed along the lines 2-2 shown in FIG. 3.
Figure 3:
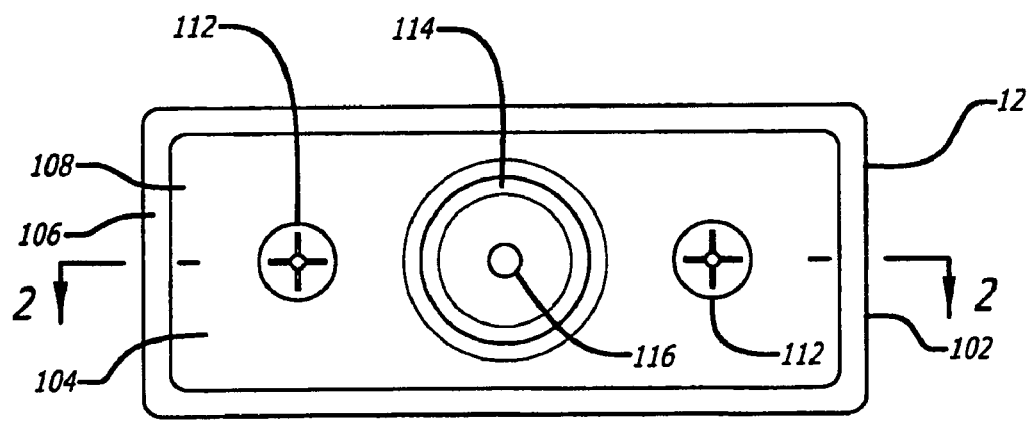
FIG. 3 shows a bottom view of an embodiment of an attachment member of a container support device.

FIGS. 2 and 3 illustrate various views of an exemplary embodiment of an attachment member for use with a container support device. As shown, the attachment member 12 includes an attachment member body 102 having an attachment member base 104 and at least one attachment member sidewall 106 in communication therewith. In the illustrated embodiment, the attachment member 12 includes four attachment member sidewalls 106 forming an attachment member recess 108. As shown, the attachment member base 104 includes at least one fastener recess 110 formed therein. The fastener recess 110 is sized to receive at least one fastener 112 therein, thereby enabling the attachment member 12 to be coupled to any number of devices. For example, in one embodiment the attachment member 12 may be coupled to a blood filtration device or extra-renal replacement therapy device. Optionally, the attachment member 12 may be coupled to any variety of devices or mechanisms as desired by the user. Referring to FIGS. 2 and 3, the fastener 112 may include a variety of fastening devices configured to couple the attachment member 12 to a support positioned on a device. Exemplary fastening devices include, without limitation, screws, bolts, pins, nails, locking members, or other mechanisms configured to couple various portions of the container support device together. In the illustrated embodiment, a rotation mount 114 is secured to a surface of the attachment member base 104 and positioned within the attachment member recess 108. The coupler recess 116 is positioned on the rotation mount 114 and configured to receive a coupler (not shown) therein, thereby permitting the joint body 14 to be movably coupled to the attachment member 12 (See FIG. 1). Optionally, the attachment member base 104 may be manufactured without a rotation mount 114 positioned within the attachment member recess 108. As such, the attachment base 104 may include a coupler recess 116 formed in the attachment member recess 108.

FIGS. 4-8 show an exemplary embodiment of a joint body for use with a container support device. As shown, the joint body 14 may include a first joint member 20 and a second joint member 22. The first joint member 20 may include a first joint body base 202 having a least one joint body sidewall 204 extending therefrom. A first joint body pin 208 may be positioned within a first joint body pin orifice 206 formed in the first joint body sidewall 204. As shown in FIGS. 4 and 5, the first joint body base 202 and the first joint body sidewall 204 form the first joint body recess 210, which is sized to receive at least a portion of the second joint body member 22 therein. The first joint body base 202 further includes a first joint body coupling port 212 formed thereon and sized to receive a first joint body coupler 214 therein. The first joint body coupler 214 may be sized to traverse the first joint body coupling port 212 located on the first joint member 20 and engage the coupler recess 116 formed on the attachment member base 104 of the attachment member 12. (See FIGS. 2 and 3). FIG. 5 shows an embodiment of the first joint member 20 having a rotation body 216 positioned on a surface of the first joint body base 202. The rotation body 216 may be sized and configured to engage the rotation mount 114 located within attachment member recess 108 of the attachment member 12 thereby permitting the first joint member 20 to rotate within the attachment member recess 108 formed on the attachment member 12 when coupled thereto. (See FIGS. 2 and 3). As such, either the rotation mount 114 of the attachment member 12, or the rotation body 216 of the first joint member 20, or both, may include any appropriate rotational devices or material to permit the rotation of the first joint member 20 when coupled to the attachment member 12. Exemplary rotational devices or materials may include, without limitation, bearings including ball bearings or cylindrical bearings, races, low or ultra low friction materials, friction reducing materials, low friction plastics or elastomers, oils, carbons, teflons, silicons, or similar friction reducing materials.

Referring again to FIGS. 4-8, the second joint member 22 includes a second joint body base 222 having at least one second joint body sidewall 224 extending therefrom. A second joint body pin 228 is positioned within a second joint body pin orifice 226 formed in at least one second joint body sidewall 224. A second joint body attachment passage 230 may be formed within or approximate to the second joint body base 222. In one embodiment, the second body attachment passage 230 may be sized and configured to receive the first joint body pin 206 therein. As shown in the illustrated embodiment, the second joint body attachment passage 230 is substantially perpendicular to the second joint body pin 228. In an alternate embodiment, the second joint body attachment passage 230 may be transverse to or co-aligned with the second joint body pin 228.

As shown in FIGS. 4 and 8, the joint body 14 is configured to permit the second joint body member 22 to freely move along the arc $A_1$ when coupled to the first joint body member 20, thereby forming a single pivot universal joint. In addition, when the support body 16 is coupled to the second joint body member 22, the support body 16 is permitted to freely move along the arc $A_2$. As shown, arc $A_2$ is substantially perpendicular to arc $A_1$. However, $A_2$ may be positioned at any angle relative to arc $A_1$. As such, the joint body 14 enables two points of freedom of rotation relative to the vertical access $A_V$. Further, the joint body 14 may be rotationally coupled to the attachment member 12 when a first joint body coupler 214 is positioned within the first joint body coupling port 212 located proximal to a rotation body 214 formed on the first joint body base 202. As a result, the joint body 14 is rotationally coupled to the attachment member 12 thereby permitting a third point of freedom of rotation relative to the vertical axis $A_V$ and eliminating or reducing constraints or torques present within the container support device 10. Those skilled in the art will appreciate that any number of joint bodies may be coupled to together to form a multiple pivot universal joint.

FIGS. 9-11 show an exemplary embodiment of a support body 16 for use with a container support device 10. In the illustrated embodiment, the support body 16 includes a main body 300 having a first coupling section 302 and a second coupling section 304 formed thereon. The first and second coupling sections 302, 304, respectively, define at least one coupling relief 306 sized to receive the second joint body pin 226 of the second joint member 22 therein. (See FIGS. 4-8). In the illustrated embodiment, two coupling reliefs 306A, 306B are formed on the support body 16. A first coupling aperture 308 may be formed on the first coupling section 302. Similarly, a second coupling aperture 310 may be formed on the second coupling section 304. The first and second coupling apertures 308, 310, respectively, are sized to receive the second joint body pin 226 therethrough. In an alternate embodiment, the first and second coupling apertures 308, 310, respectively, may be sized to receive a fastening device configured to couple to the second joint member 22 therein. Exemplary fastening devices include, without limitation, pins, screws, hooks, eye bolts, washers or similar devices. Optionally, any number of coupling sections and coupling apertures are also within the scope of the invention. Similarly, the main body 300 may be attached to the joint body 14 using any other methods known to those skilled in the art without the use of coupling apertures. A container support body 312 is secured to the main body 300 and includes at least one container support 18 positioned thereon. In one embodiment, the container support body 312 may be securely attached or immovably attached to the main body 300. For example, the container support body 312 may be welded to or otherwise secured to the main body 300. In an alternate embodiment, the container support body 312 may be detachably coupled to the main body 300. For example, the container support body 312 may be coupled to the main body in screw-fit relation. Optionally, any number of detachable coupling methods may be used to couple the container support body 312 to the main body 300, including, without limitation, snap fit relation, pinned relations, and friction fit relation. Optionally, the container support body 312 may be immovably or non-rotatably coupled to the main body 300. In an alternate embodiment, the container support body 312 may be capable of rotating about the vertical axis $A_V$ of the container support device 10.

Referring again to FIGS. 9-11, the illustrated embodiment shows four container supports 18 positioned on the container support body 312. Optionally, any number of container supports 18 may be positioned on the container support body 312. For example, the container support body 312 may include two container supports 18. Further, when multiple container supports 18 are positioned on the container support body 312, the container supports 18 may be of constant or variable width, length, pitch, angle, or orientation. As shown in FIG. 10, the container supports 18 may be immovably or non-rotatably affixed to the container support body 312. For example, the container supports 18 may be coupled to the container support body 312 using, without limitation, screws, threads, bolts, pins, welds, adhesives, or any combination thereof. In an alternate embodiment, FIG. 11 shows a container support 18 affixed to the container support body 312 in moveable relation. For example, the container supports 18 may be capable of rotating about the container support access As In the illustrated embodiment, the container supports 18 comprise cylindrical body members affixed to the container support body 312. Optionally, the container supports 18 may be formed in a variety of shapes including, straight members, curved members, clips, hooks, bottle supports, cups or similar shapes. In the embodiment illustrated in FIG. 9, the container supports 18 are positioned an equal distance from the vertical access $A_V$ of the support body 16. As a result, when equally weighted material containers are positioned on opposing container supports 18, the support body 16 will be balanced along the vertical axis $A_V$. Optionally, the container supports 18 may be positioned at equal or unequal distances from the vertical axis $A_V$ of the support body 16. In addition, the container supports 18 may be positioned on the container support body 312 so as to remain balanced in relation to the vertical axis $A_V$.

FIGS. 12-14 show an alternate embodiment of a container support body for use with a container support device 10. Similar to the embodiment illustrated in FIGS. 9-11, the container support body 412 is secured to the main body 300 and includes at least one container support 418 positioned thereon. In the illustrated embodiment the container support body 412 includes a container support channel 420 formed therein. The container support channel may be sized to receive at least a portion of the container support 418 therein and configured to permit the container support 418 to be selectively moved and repositioned therein by a user. In an exemplary embodiment, the container support channel 420 formed in the support body 412 includes at least one movable coupling member 422 therein. A coupling fastener 424 may be coupled to or attachable to either the coupling member 422, the container support 418, or both. As such, the container support 418 may include a fastener recess 426 sized to receive a fastening coupler 424 therein. During use, the user may position the coupling member 422 at a desired position on the container support 412 (See line 1 in FIG. 12). Thereafter, the user may couple the container support 418 to the coupling member 422, thereby compressing the container support body 412 between the container support 418 and the coupling member 422 and restricting the movement of the coupling member 422 within the container support channel 420. As a result, the container support 418 is secured to the container support body 412 at location desired by the user. Any number of container supports 418 may be positioned on or detachably coupled to the container support body 412. For example, the container support body 412 may include two container supports 418. Further, when multiple container supports 418 are positioned on the container support body 412, the container supports 418 may be of constant or variable width, length, pitch, angle, or orientation. In the illustrated embodiment, the container support channel 420 is horizontally positioned on the container support body 412. In an alternate embodiment, the container support body 412 may include any vertically positioned container support channels, horizontally positioned container support channels, container support channels positioned at an angle, or any combination of the above.

In closing, it is noted that specific illustrative embodiments of the container support device have been disclosed hereinabove. However, it is to be understood that the container support device is not limited to these specific embodiments and not limited to the precise embodiments described in detail hereinabove.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A blood cleansing system comprising:
   a weight scale;
   a container support device for supporting at least one container of a blood treating fluid, wherein the container support device includes:
   an attachment member for coupling the container support device to the weight scale;
   a joint body attached to the attachment member and configured to rotate about an axis of the attachment member;
   a support body secured to the joint body; and
   at least two container supports extending from the support body, wherein the container supports are (i) spaced equidistant from an axis of the support body, and (ii) configured to each stably support the at least one container of blood treating fluid.

2. The blood cleansing system of claim 1, wherein the attachment member includes an attachment member base, a rotation mount positioned on the attachment member base, the rotation mount rotatably coupled to the joint body.

3. The blood cleansing system of claim 1, wherein the joint body includes a first joint member rotatably coupled to a second joint member.

4. The blood cleansing system of claim 3, wherein the first joint member includes a joint body base having a rotation body located thereon.

5. The blood cleansing system of claim 1, wherein the joint body includes a universal joint assembly.

6. The blood cleansing system of claim 5, wherein the universal joint assembly includes a block and pin universal joint.

7. The blood cleansing system of claim 5, wherein the universal joint assembly includes at least one of:
   (i) a single pivot joint;
   (ii) a double pivot joint; and
   (iii) a multiple pivot joint.

8. The blood cleansing system of claim 1, wherein the at least two container supports are integrally formed with the support body.

9. The blood cleansing system of claim 1, wherein the at least two container supports are rotatably or moveably coupled to the support body.

10. The blood cleansing system of claim 1, which includes a container support channel formed in the support body, the container support channel configured to receive the container supports.

11. The blood cleansing system of claim 1, wherein the blood cleansing system is one of a haemofiltration, haemodialysis, haemodiafiltration, or plasmatheresis system.

12. A blood cleansing system comprising:
   a weight scale;
   at least two container supports, each support configured to support a container of a blood therapy fluid;
   a support body supporting the at least two container supports, wherein the at least two container supports are spaced equidistantly about an axis through the support body;
   a joint body securing the support body; and
   an attachment member securing the joint body to the weight scale, the joint body configured to rotate about an axis of the attachment member;
   wherein: (i) the joint body is configured to move along a first arc and the support body is configured to move along a second arc, and (ii) the second arc has an axis of rotation that is generally perpendicular to an axis of rotation of the first arc.

* * * * *